United States Patent
Zhang et al.

(10) Patent No.: US 7,495,772 B2
(45) Date of Patent: Feb. 24, 2009

(54) MULTI-CAVITY FABRY-PEROT INTERFEROMETRIC THIN-FILM SENSOR WITH BUILT-IN TEMPERATURE COMPENSATION

(75) Inventors: Yan Zhang, Blacksburg, VA (US); Kristie L. Cooper, Blacksburg, VA (US); Anbo Wang, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 352 days.

(21) Appl. No.: 11/413,119

(22) Filed: Apr. 28, 2006

(65) Prior Publication Data

US 2007/0115480 A1 May 24, 2007

Related U.S. Application Data

(60) Provisional application No. 60/739,008, filed on Nov. 23, 2005.

(51) Int. Cl.
 *G01B 11/02* (2006.01)
 *G01B 9/02* (2006.01)
 *G01B 11/28* (2006.01)
(52) U.S. Cl. ............... 356/503; 356/630; 356/519; 356/480
(58) Field of Classification Search ............ 356/480, 356/519, 503, 504, 630, 632
 See application file for complete search history.

(56) References Cited

U.S. PATENT DOCUMENTS

| 4,627,728 A * | 12/1986 | Willson ............. 356/480 |
|---|---|---|
| 6,744,522 B2 * | 6/2004 | De Groot et al. ......... 356/503 |
| 7,268,884 B2 * | 9/2007 | Kringlebotn et al. ...... 356/477 |
| 2002/0145739 A1 * | 10/2002 | De Groot et al. ......... 356/503 |
| 2005/0134861 A1 * | 6/2005 | Kringlebotn et al. ...... 356/480 |
| 2005/0254062 A1 * | 11/2005 | Tan et al. ................ 356/480 |

OTHER PUBLICATIONS

Zhang et al., "Multicavity Fabry-Perot Interferometric Thin-Film Sensor with Built-In Temperature Compensation"; IEEE Photonics Technology Letters, vol. 17, No. 12, pp. 2712-2714; Dec. 2005.
Zhang et al., "Miniature Fiber-Optic Multicavity Fabry-Perot Interferometric Biosensor"; Optics Letters, vol. 30, No. 9, pp. 1021-1023; May 1, 2005.

* cited by examiner

*Primary Examiner*—Patrick J Connolly
(74) *Attorney, Agent, or Firm*—Whitham Curtis Christofferson & Cook, PC

(57) ABSTRACT

A fiber optic sensor includes at least two Fabry-Perot (FP cavities) defined by at least three partially reflecting surfaces which individually and together are capable of generating different interference spectra which are affected by temperature. One of the FP cavities is formed at an end of the sensor and includes a surface which is capable of supporting a thin film, the optical thickness of which is to be measured. The other FP cavity between the lead-in fiber and the first FP cavity thus does not include the film and can thus independently provide highly accurate temperature information for calibrating the optical length of the second FP cavity and compensation for temperature effects on measurement of the thin film supported thereon, preferably by subtraction of a calibrated temperature-dependent change in optical length of the second FP cavity from the measurement made.

20 Claims, 1 Drawing Sheet

MULTI-CAVITY FABRY-PEROT INTERFEROMETRIC THIN-FILM SENSOR WITH BUILT-IN TEMPERATURE COMPENSATION

CROSS-REFERENCE TO RELATED APPLICATIONS

This application claims benefit of priority of U.S. Provisional Patent Application Ser. No. 60/739,008, filed Nov. 23, 2005, which is hereby fully incorporated by reference.

BACKGROUND OF THE INVENTION

1. Field of the Invention

The present invention generally relates to fiber optic sensors and, more particularly, to temperature compensation of fiber optic sensors employing self-assembled thin films.

2. Description of the Prior Art

There has been much recent interest in fiber-optic devices using so-called self-assembled multi-layer thin films. These sensors using self-assembled multi-layer thin films function by reflecting or scattering light to the cladding which is formed of the self-assembled thin films (which are easily and rapidly formed with excellent uniformity and repeatability by alternate immersion in any of a wide variety of cationic and anionic solutions at room temperature) and sensing is accomplished by detection of change in transmitted or reflected light due to changes in the optical thickness of a coating such as cladding. (Optical thickness is a function of actual or physical thickness; differing therefrom by a factor which is the index of refraction of the material.) Therefore, such sensors are particularly well-adapted to detection of the presence of chemical and biological materials in the environment of the sensor which may be absorbed, adsorbed or otherwise bound, possibly selectively, to or in the coating which thus changes the physical and/or optical thickness of the coating, leading to many potential applications in medicine, biotechnology and national security for detection of, for example, DNA hybridization or bacteria detection or even for the study of self-assembled thin-films themselves and their formation. Such sensing and/or measurement using sensors including self-assembled multi-layer thin films is more rapid than other material detection techniques and the signals produced by such sensors are stable with high visibility. By the same token, however, these mechanisms providing high sensitivity to the optical thickness of thin films (which also makes such sensors useful for the study of the thin films themselves) also provide high sensitivity to temperature changes which may be useful for temperature measurements but may be a source of error for other parameters of interest such as the presence of particular materials. The existence of such a potential source of error compromises both sensitivity and specificity of the sensor and, indeed, it has been necessary in some applications to increase the concentration of a material for it to be reliably detected.

Within the area of biological material detectors, it is known to use labels (e.g. fluorescence) for particular materials. However, the use of such labels may interfere with a process being monitored, such as the evolution of a material during a chemical reaction, in ways which may not be predictable and, in any event, detection of a label, at best, provides only an indirect measurement of the parameter of interest. Therefore, there is interest in developing sensors for chemical and biological materials which do not require use of a label, referred to as label-free detection.

SUMMARY OF THE INVENTION

It is therefore an object of the present invention to provide a thin-film fiber-optic sensor having built-in temperature compensation.

It is another object of the invention to provide a sensitive detector for the presence of selected materials which does not require labeling of the selected material.

In order to accomplish these and other objects of the invention, a multi-cavity Fabry-Perot (FP) structure is provided in the fiber-optic structure forming the thin-film sensor. Such a multi-cavity FP structure has at least three reflecting surfaces and can be arranged such that the dimensions of the cavities and thus the distance between reflecting surfaces will vary with temperature while one of the surfaces at the end of the fiber-optic element can have a thin film formed thereon in accordance with a material or parameter of interest. The temperature compensation capability can be enhanced by selection of different cavity materials and may preferably be applied by extraction of temperature information from the cavities multiplexed (e.g. by time or wavelength) with extracting of information from the thin film or calibrating the sensor in regard to temperature using a separate sensor.

In accordance with one aspect of the invention, a sensor and sensor system providing temperature compensation for a measurement of an optical thickness of a film are provided including a sensor comprising at least three partially reflecting surfaces defining at least first and second Fabry-Perot cavities exhibiting different indices of refraction, one of the partially reflecting surfaces being at an end of the sensor and including a surface associated with the second Fabry-Perot cavity for supporting a film, the optical thickness of which is to be measured wherein temperature information is independently provided by the first Fabry-Perot cavity for temperature compensation of measurements made using an interference spectrum produced by the second Fabry-Perot cavity and/or a combination of the first and second Fabry-Perot cavities.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1A:
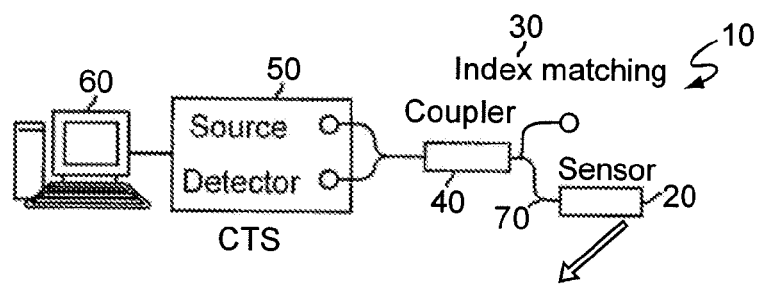
FIGS. 1A and 1B are generalized schematic diagrams of a multi-cavity FP interferometric sensor (MFPI) system and an MFPI sensor, respectively, in accordance with the invention.
Figure 1B:
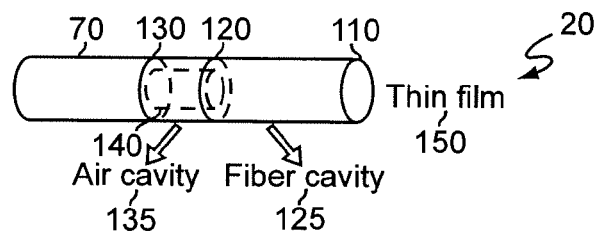

Referring now to the drawings, and more particularly to FIGS. 1A and 1B, there is schematically shown a multi-cavity Fabry-Perot interferometric (MFPI) sensor in accordance with a preferred embodiment of the invention. The MFPI sensor is distinguished by its simplicity, small size, high sensitivity, low cost and capability of measurement of ultra-thin films. Such thin films are normally characterized by x-ray scattering, near-field scanning optical microscopy, atomic force microscopy and other complex and costly laboratory techniques. However, since the changes in optical cavity length induced by the thermo-optic effect and thermal expansion have significant influence on measurement accuracy using MFPI sensors, it is necessary to introduce temperature compensation in order to perform high accuracy measurements at varying temperatures. The overall system shown in FIG. 1A is similar to some known systems and preferably includes a MFPI sensor 20, significant details of which are illustrated in FIG. 1B and discussed below, an index matching arrangement 30, a fiber optic coupler 40, a light source and light detector arrangement for directing light into the optical fiber coupler 40 and detecting light reflected by the sensor 20 through optical fiber 70 and some form of output device 60 such as a computer or terminal. All of these elements are known in numerous forms to those skilled in the art and details thereof are not critical to the successful practice of the invention.

Elements of sensor 20 which are important to the practice of the invention are shown in FIG. 1B. A key to the invention is that the sensor should have at least three semi-reflecting surfaces 110, 120 and 130 which are preferably formed by an abrupt change in index of refraction of the materials on either side of a preferably planar interface at each of those locations but such interfaces can be formed in many ways and with many different materials as will be evident to those skilled in the art. These partially reflecting surfaces define regions 125, 135, referred to as cavities and do not necessarily require that any such cavity be formed as an air gap although an air gap is considered preferable for cavity 135 for at least simplicity of manufacture and to allow freedom of choice of material and its coefficient of thermal expansion (CTE) for the structure establishing the air gap such as a capillary tube.

Generally, Fabry-Perot interferometric (FPI) sensors are designed as single cavity sensors. A simple, low-finesse FP cavity can be directly formed by the cleaved end faces of the lead in fiber (e.g. 70 and a reflection fiber, the fibers being spaced from each other by bonding to silica capillary tubing such as is schematically indicated by the annular region 140 in FIG. 1B. The reflection from the far end of the reflection fiber is generally minimized so that multiple interferences are reduced and, effectively, only one cavity is presented.

In contrast, in a MFPI sensor in accordance with the present invention, the reflection fiber is short so that the reflection from the far end of the reflection fiber is strong and at least two cavities 125, 135 defined by three partially reflecting surfaces are presented. While it is preferred to use a reflecting fiber to form one of the FP cavities, it should be understood that a thin film of interest can also form an extrinsic FP cavity if the wavelength of the probe light is comparable to the film thickness, usually in a micrometer or sub-micrometer range. In either case, the optical thickness of the film can be measured by monitoring reflection power. The combination of cavities 125 and 135 also effectively presents a third cavity and thus each of three possible pairs of reflecting surfaces (e.g. 110-120, 120-130 and 110-130) will cause a distinctive interference pattern yielding a reflection spectrum due to the multiple interferences resulting from a multicavity sensor 20. Moreover, any change in any the cavities such as a change in dimensions or adsorption of thin films (e.g. 150) will change the reflection spectrum. Thus it is possible to measure the thickness of thin films during such an adsorption process such as polymer self-assembly and immunosensing.

The thin film sensing is based on the measurement of optical thickness changes of the fiber-film cavity caused by the adsorption of target molecules. The adsorbed thin film can be estimated as an extension of the fiber cavity 125 when the refractive index of the film is close to the refractive index of the reflection fiber (and the material of the reflection fiber chosen accordingly). High sensitivity can be achieved due to the intrinsic nature of FP interferometry and measurements to 0.1 nm have been achieved. However, the optical thickness of the fiber cavity is also highly dependent on the environment temperature due to the thermo-optic effect and thermal expansion. The change in the optical thickness of the fiber cavity 125 can be expressed as $$\Delta(nd)_f = \Delta n_f \cdot d_f + \Delta d_f \cdot n_f \quad (1)$$
$$= \alpha_n \Delta T \cdot d_f + \alpha_d d_f \Delta T \cdot n_{f+}$$
$$= \alpha_f n_f d_f \Delta T$$

where $\alpha_n$ is the thermo-optic coefficient, $\alpha_d$ is the thermal expansion coefficient, $\alpha_f = \alpha_n/n_f + \alpha_d$ is the effective temperature coefficient. For fused silica corresponding coefficients values are $\alpha_n = 1.0 \times 10^5/°$ C., $\alpha_d = 5.5 \times 10^{-7}/°$ C., and $\alpha_f = 7.4 \times 10^{-6}/°$ C. ($n_f = 1.457$, $\lambda = 0.633$ nm). It is seen that the thermo-optic effect is the dominant noise factor in the optical thickness measurement and is more than ten times larger than the effect of the thermal expansion. Therefore any non-linearity of the thermal expansion effect can be neglected in the above equations. However, it is also clear from the above analysis that any variation in the environmental temperature will affect the accuracy of the thin-film measurement. In particular, when the fiber cavity is longer, the absolute change in optical thickness will be correspondingly greater and more sensitive to temperature variation. For example, for an MFPI sensor with a 100 μm fiber cavity, the variation in optical thickness over a 100° C. temperature excursion for an uncompensated sensor is approximately 100 nm which is far too large for accurate thin film measurement. While this variation in optical thickness with temperature can be reduced by using a shorter reflection fiber, as is preferred but achieved only with substantially increased difficulty, the shortest practically achieved reflection fibers will still compromise measurement accuracy.

The length of the air cavity also changes with temperature due to expansion of the preferably silica capillary tube 140. Therefore, it is possible to compensate the temperature dependence of the fiber cavity by extracting temperature information from the air cavity independently of other cavities. The change in thickness/length of the air cavity with temperature can be estimated as $$\Delta d_a = (\alpha_d \Delta T + \beta_d \Delta T^2) d_a \quad (2)$$

where $\alpha_{d+}$ and $\beta_d$ are the thermal expansion coefficients of the capillary tube and $d_a$ is the thickness of the air cavity. Here the non-linearity of the thermal expansion effect is preferably considered for better fitting.

It can also be appreciated from this latter equation (2) that the temperature sensitivity is related to the thermal expansion coefficients and the thickness of the air cavity. Due to the low thermal expansion coefficient of silica, a longer air cavity is preferred for temperature measurement. However, the visibility of the interference fringes will be impaired by the coupling loss from a long air cavity. Thus the optimum thickness of the air cavity is considered to be approximately 100 μm.

It is easier to calculate the lengths of the air cavity and the fiber cavity from the resulting interference patterns if they can be separated in the frequency domain, which is similar to the demodulation of a frequency-based multiplexed sensor. Therefore, the optical length of the fiber cavity can be fabricated several times longer than the air cavity and interference patterns observed at different wavelengths, preferably proportional to the ratio of cavity lengths. Exemplary dimensions which have been successfully used experimentally are an air cavity length of 133 μm and a fiber cavity optical length of 242 μm in a MFPI sensor which was fabricated by fusion splicing a silica capillary tube between the lead-in and reflection fibers as described above.

The ability to provide substantially complete temperature compensation in accordance with the invention as described above has been experimentally verified using system apparatus substantially as shown in FIG. 1A, described above. The reflection spectrum of the sensor was monitored by a component testing system (CTS) and analyzed using a personal computer. The tunable laser of the CTS was coupled into the sensor and the reflection signal was routed back to the CTS detector through the same coupler (e.g. 40). The laser wavelength range was 1520 to 1570 nm with an accuracy of 1 pm.

Multiple beam interference from the MFPI sensor as described above, can be evaluated by matrix formalism. The reflectance for the multicavity sensor is $$R = \frac{R_1 + R_2 + R_3 + R_1 R_2 R_3 - 2\sqrt{R_1 R_2}\,(R_3 + 1)\cos(2\beta_2) - 2\sqrt{R_2 R_3}\,(R_1 + 1)\cos(2\beta_3) + 2\sqrt{R_1 R_3}\,\cos 2(\beta_2 + \beta_3) + 2\sqrt{R_1 R_3}\,R_2 \cos 2(\beta_2 - \beta_3)}{1 + R_1 R_2 + R_2 R_3 + R_1 R_3 - 2\sqrt{R_1 R_2}\,(R_3 + 1)\cos(2\beta_2) - 2\sqrt{R_2 R_3}\,(R_1 + 1)\cos(2\beta_3) + 2\sqrt{R_1 R_3}\,\cos 2(\beta_2 + \beta_3) + 2\sqrt{R_1 R_3}\,R_2 \cos 2(\beta_2 - \beta_3)} \quad (3)$$

where $R_1$, $R_2$ and $R_3$ are the reflection coefficients of the interfaces/surfaces 110, 120, 130, respectively, and $\beta_2$ and $\beta_3$ are the phase shifts of the air and fiber cavities as set out in the above-incorporated U.S. Provisional Patent Application or by other computational techniques of fitting the reflection spectrum observed with the theoretical model. By doing so, the cavity length can be demodulated with up to 0.1 nm resolution (which is limited by the CTS) which corresponds to 2° C. temperature resolution.

Figure 2:
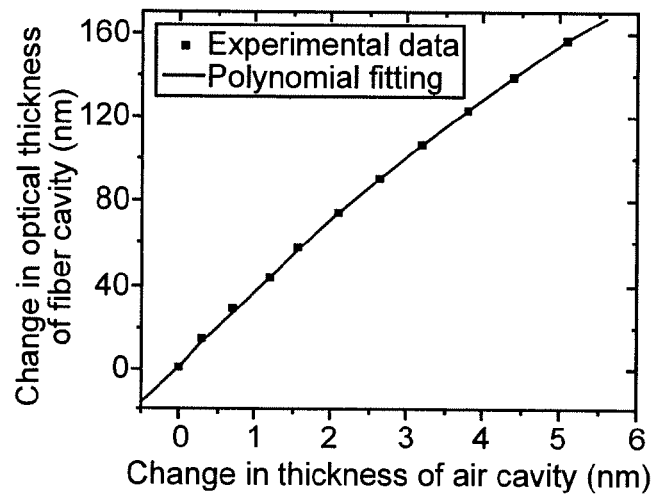
FIG. 2 is a graphical depiction of changes in air cavity thickness to the fiber cavity optical thickness of a MFPI sensor over a temperature range of 0° to 100° Centigrade.

The sensor was first calibrated in an environmental chamber and the relative changes in air cavity thickness and fiber cavity optical thickness are graphically depicted in FIG. 2, which can be fit to a polynomial. The air cavity 135 thickness depends on the thermal expansion of the silica tube but is independent of and decoupled from any adsorption or other thin film at the end surface of the sensor at the end of the fiber cavity 125. Therefore, temperature information can be independently extracted from the air cavity and used to compensate thermo-optic and thermal expansion effects of temperature on the fiber cavity.

Figure 3:
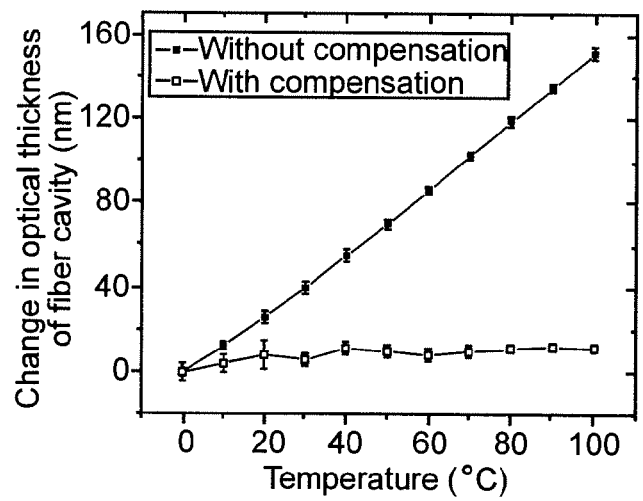
FIG. 3 is a graphical depiction of changes in optical thickness of a fiber/film cavity over the same temperature range as in FIG. 2, establishing the capability of the invention to provide substantially complete temperature compensation.

An experimental measurement of film thickness was performed with a self-assembled film measured to be 86 nm thick at room temperature (25° C.) by comparing the fiber film cavity with the bare fiber cavity. Since the film is much thinner than the fiber cavity, any variation in the environmental temperature will affect measurement accuracy in the thin-film measurement due to the thermal effects on the fiber cavity. As shown in FIG. 3, the optical thickness of the fiber-film cavity changes more than 150 nm (nearly twice the film thickness in this case) over the temperature range from 0° to 100° C. although the changes are principally due to the thermo-optic effect and thermal expansion of the fiber cavity 125, itself, which make the measurement of an ultra-thin film difficult under conditions of temperature variation. However, as also shown in FIG. 3, these changes may be subtracted by introducing the temperature information derived from the air cavity 135. After compensation in this manner, the film thickness was measured to be 87±2 nm over the entire temperature range (n=1.54). Some component of even this very slight variation in the measurement data after compensation may come from thickness changes in the thin film due to temperature (note the slight upward trend in the measurement with temperature) and/or relative humidity variations.

In view of the foregoing, it is clearly seen that substantially full temperature compensation of a sensor is provided which is applicable to sensors using multi-layer self-assembling films which have properties favoring applications to chemical and biological material detection as well as providing a sensor for the study of properties of thin films themselves and their formation and under a wide range of environmental temperatures. Further, the sensor provides highly sensitive detection of selected materials, even at low concentrations and without a need for labeling materials of interest.

While the invention has been described in terms of a single preferred embodiment, those skilled in the art will recognize that the invention can be practiced with modification within the spirit and scope of the appended claims.

The invention claimed is:

1. A sensor providing temperature compensation for a measurement of an optical thickness of a film, said sensor comprising at least three partially reflecting surfaces defining at least first and second Fabry-Perot cavities exhibiting different indices of refraction, one of said partially reflecting surfaces being at an end of said sensor and including a surface associated with said second Fabry-Perot cavity for supporting a film, the optical thickness of which is to be measured, wherein temperature information is independently provided by said first Fabry-Perot cavity for temperature compensation measurements made using an interference spectrum produced by said second Fabry-Perot cavity and/or a combination of said first and second Fabry-Perot cavities.

2. A sensor as recited in claim 1, wherein said second Fabry-Perot cavity comprises a reflection fiber.

3. A sensor as recited in claim 1, wherein said second Fabry-Perot cavity consists of a thin film.

4. A sensor as recited in claim 1, wherein said interference spectrum is obtained for each or said first and second Fabry-Perot cavities by time multiplexing.

5. A sensor as recited in claim 1, wherein said interference spectrum is obtained for each or said first and second Fabry-perot cavities by wavelength multiplexing.

6. A sensor as recited in claim 1, wherein said first Fabry-Perot cavity is an air cavity.

7. A sensor as recited in claim 6, wherein said air cavity is defined between a lead-in fiber and a reflection fiber by a silic capillary tube.

8. A sensor as defined in claim 1, wherein said second Fabry-Perot cavity is longer than said first Fabry-Perot cavity.

9. A sensor as recited in claim 1, wherein said film is a multi-layer self-assembled film.

10. A sensor system providing temperature compensation for a measurement of an optical thickness of a film, said sensor system comprising a sensor having at least three partially reflecting surfaces defining at least first and second Fabry-Perot cavities exhibiting different indices of refraction, one of said partially reflecting surfaces being at an end of said sensor and including a surface associated with said second Fabry-Perot cavity for supporting a film, the optical thickness of which is to be measured, wherein temperature information is independently provided by said first Fabry-Perot cavity for temperature compensation of measurements made using an interference spectrum produced by said second Fabry-Perot cavity and/or a combination of said first and second Fabry-Perot cavities.

11. A sensor system providing temperature compensation for a measurement of an optical thickness of a film, said sensor system comprising a sensor having at least three partially reflecting surfaces defining at least first and second Fabry-Perot cavities exhibiting different indices of refraction, one of said partially reflecting surfaces being at an end of said sensor and including a surface associated with said second Fabry-Perot cavity for supporting a film, the optical thickness of which is to be measured, wherein said second Fabry-Perot cavity comprises a reflection fiber and a calibrated change in length of said second Fabry-Perot cavity corresponding to said temperature information is subtracted from a measured optical length of said second Fabry-Perot cavity.

12. A sensor system as recited in claim 10, wherein said second Fabry-Perot cavity consists of a thin film.

13. A sensor system as recited in claim 10, wherein said interference spectrum is obtained for each or said first and second Fabry-Perot cavities by time multiplexing.

14. A sensor system as recited in claim 10, wherein said interference spectrum is obtained fore each or said first and second Fabry-perot cavities by wavelength multiplexing.

15. A sensory system as recited in claim 10, wherein said first Fabry-Perot cavity is an air cavity.

16. A sensor system as recited in claim 15, wherein said air cavity is defined between a lead-in fiber and a reflection fiber by a silic capillary tube.

17. A sensory system as defined in claim 10, wherein said second Fabry-Perot cavity is longer than said first Fabry-Perot cavity.

18. A sensor system as recited in claim 10, wherein said film is a multi-layer self-assembled film.

19. A sensor system as recited in claim 11, wherein said first Fabry-Perot cavity is an air cavity.

20. A sensor system as recited in claim 19, wherein said air cavity is defined between a lead-in fiber and a reflection fiber by a silica capillary tube.

* * * * *